US007662393B2

(12) United States Patent
Arvinte et al.

(10) Patent No.: US 7,662,393 B2
(45) Date of Patent: Feb. 16, 2010

(54) LIQUID GROWTH HORMONE FORMULATION AND METHOD OF USE

(75) Inventors: Tudor Arvinte, Riehen (CH); Karnine Luet Kleiber, Feigères (FR)

(73) Assignee: Ares Trading S.A., Aubonne (CH)

( * ) Notice: Subject to any disclaimer, the term of this patent is extended or adjusted under 35 U.S.C. 154(b) by 98 days.

(21) Appl. No.: 11/578,136

(22) PCT Filed: Mar. 30, 2005

(86) PCT No.: PCT/EP2005/051448

§ 371 (c)(1),
(2), (4) Date: Oct. 10, 2006

(87) PCT Pub. No.: WO2005/105148

PCT Pub. Date: Nov. 10, 2005

(65) Prior Publication Data

US 2008/0038292 A1 Feb. 14, 2008

(30) Foreign Application Priority Data

Apr. 7, 2004 (EP) .................................. 04101444

(51) Int. Cl.
*A61K 38/27* (2006.01)
*A01N 38/00* (2006.01)
*A61K 38/25* (2006.01)
(52) U.S. Cl. .......................... 424/198.1; 514/12; 514/2; 530/399
(58) Field of Classification Search ....................... None
See application file for complete search history.

(56) References Cited

U.S. PATENT DOCUMENTS

| 4,637,834 | A | | 1/1987 | Thurow | |
|---|---|---|---|---|---|
| 5,017,609 | A | * | 5/1991 | Escobar et al. | 514/538 |
| 5,461,030 | A | * | 10/1995 | Lindenbaum | 514/4 |
| 5,567,677 | A | | 10/1996 | Castensson et al. | |
| 5,597,802 | A | | 1/1997 | Clark et al. | |
| 6,759,393 | B1 | * | 7/2004 | Morsey et al. | 514/44 |
| 2003/0190291 | A1 | * | 10/2003 | Stevenson et al. | 424/46 |
| 2006/0252682 | A1 | * | 11/2006 | Donati et al. | 514/12 |

FOREIGN PATENT DOCUMENTS

| EP | 0131864 A2 | | 7/1984 |
|---|---|---|---|
| EP | 0211601 A2 | | 7/1986 |
| WO | 9319776 A1 | | 10/1993 |
| WO | 9403198 A1 | | 2/1994 |
| WO | 9729767 A1 | | 8/1997 |
| WO | WO/97/39768 | * | 10/1997 |
| WO | WO/01/03741 | * | 1/2001 |
| WO | WO/2004/004780 | * | 1/2004 |

OTHER PUBLICATIONS

Altschul, S.F. et al., "Basic Local Alignment Search Tool", J. Mol. Biol., 215:403-410 (1990).
Altschul, S.F. et al., "Gapped BLAST and PSI-BLAST: A New Generation of Protein Database Search Programs", Nucleic Acids Research, 23:3389-1402 (1997).
Becker, G.W. et al., "Isolation and Characterization of a Sulfoxide and a Desamido Derivative of Biosynthetic Human Growth Hormone", Biotechnology and Applied Biochemistry, 10:326-327 (1988).
Bewley, T.A. et al., "Sequence Comparison of human Pituitary Growth Hormone, Human Chorionic Somatomammotropin, and Ovine Pituitary Growth and Lactogenic Hormones", Int. J. Peptide Res., 4:281-287 (1972).
Chen, E.Y. et al., "The Human Growth Hormone Locus: Nucleotide Sequence, Biology, and Evolution", Genomics, 4:479-497 (1989).
Devereux, J. et al., "A Comprehensive Set of Sequence Analysis Programs for the VAX", Nucleic Acids Research, 12:387-395 (1984).
Gertler, A. et al., "Inhibition of Lactogenic Activities of Ovine Prolactin and Human Growth Hormone (hGH) by a novel Form of a Modified Recombinant hGH", Endocrinology, 118:720-726 (1986).
Goeddel, S. V. et al., "Direct Expression in *Escherichia coli* of a DNA Sequence Coding for Human Growth Hormone", Nature, 281:544-548 (1979).
Graf, L. et al., "Human Somatotropin Selective Removal with Trypsin of Residues 135-145 from the Hormone Molecule with no Loss of Biological Activities", The Journal of Biological Chemistry, 257:2365-2369 (1982).
Grantham, R., "Amino Acid Difference Formula to Help Explain Protein Evolution", Science, 185:862-864 (1974).
Hsiung, H. M. et al., "Use of Bacteriocin Release Protein in *E. coli* for Excretion of Human Growth Hormone into the Culture Medium", Biotechnology, 7:267-271.

(Continued)

*Primary Examiner*—Lorraine Spector
*Assistant Examiner*—Elly-Gerald Stoica
(74) *Attorney, Agent, or Firm*—Browdy and Neimark, PLLC

(57) ABSTRACT

The invention relates to a liquid formulation comprising a growth hormone or a substance, which stimulates release or potentiates the activity of endogenous hGH; a polyethylene-polypropylene glycol; a citrate/phosphate buffer, an alkali metal salt and an alkaline earth metal salt or a pseudo alkaline earth metal salt, and to a process of preparation thereof.

28 Claims, No Drawings

OTHER PUBLICATIONS

Jorgensen, K.D. et al., "Pharmacokinetics of Biosynthetic and Pituitary Human Growth Hormones in Rats", Pharmacology & Toxicology, 63:129-134 (1988).

Kramer, M. S. et al., "Distinct Mechanism for Antidepressant Activity by Blockade of Central Substance P Receptors", Science, 281:1640-1645 (1998).

Lewis, U.J. et al., "Enhancement of the Hyperglycemic Activity of human Growth Hormone by Enzymic Modification", Endocrinology, 101:1587-1603 (1977).

Lewis, U.J. et al., "Human Growth Hormone: Additional Members of the Complex", Endocrinology, 104:1256-1265 (1979).

Lewis, U.J. et al., "The 20,000-Dalton Variant of Human Growth Hormone: Location of the Amino Acid Deletions", Biochemical and Biophysical Research Communications, 92:511-516 (1980).

Lewis, U.J. et al., "Altered Proteolytic Cleavage of Human Growth Hormone as a Result of Deamidation", The Journal of Biological Chemistry, 256-:11645-11650 (1981).

Martial, J. A. et al., "Human Growth Hormone: Complementary DNA Cloning and Expression n Bacteria", Science, 205:602-607 (1979).

Meinkoth, J. et al., "Hybridization of Nucleic Acids Immobilized on Solid Supports", Analytical Biochmistry, 138:267-284 (1984).

Moore, J.A. et al., "Equivalent Potency and Pharmacokinetics of Recombinant Human Growth Hormones with or without an N-Terminal Methionine", Endocrinology, 122:2920-2926 (1988).

Pearson, W. R. et al., "Improved Tools for Biological Sequence Comparison", Proc. Natl. Acad. Sci. USA, 85:2444-2448 (1988).

Pearson, W. R., "Rapid and Sensitive Sequence Comparison with FASTP and FASTA", Methods in Enzymology, 183:63-98 (1990).

Singh, R. N. P. et al., "Modified Forms of Human Growth Hormone with Increased Biological Activities", Endocrinology, 94:883-891 (1974).

Smith, T.F. et al., "Identification of Common Molecular Subsequences", J. Mol. Biol., 147:195-197 (1981).

Thorlacius-Ussing, O. "Zinc in the Anterior Pituitary of Rat: A Histochemical and Analytical Work", Neuroendocrinology, 45:233-242 (1987).

Lewis et al., "A Naturally Occurring Structural Variant of Human Growth Hormone", The Journal of Biological Chemistry, 253:2679-2687 (1978).

* cited by examiner

LIQUID GROWTH HORMONE FORMULATION AND METHOD OF USE

FIELD OF THE INVENTION

The present invention relates to liquid growth hormone (GH) formulations, and in particular to liquid formulations of human growth hormone (hGH) with improved chemical and physical stability. The liquid growth hormone (GH) formulations of the present invention may be stored for a prolonged period of time at room temperature. The present invention further relates to a process for the preparation of such liquid GH formulations, and to a form of presentation thereof.

BACKGROUND OF THE INVENTION

Human growth hormone (hGH), also known as somatropin (INN) or somatotropin, is a protein hormone produced and secreted by the somatotropic cells of the anterior pituitary. Human growth hormone plays a key role in somatic growth in childhood and in metabolism in adulthood through its effects on the metabolism of proteins, carbohydrates and lipids.

Human growth hormone is a single polypeptide chain of 191 amino acids (Bewly et al, 1972) having two disulfide bonds, one between Cys-53 and Cys-165, forming a large loop in the molecule, and the other between Cys-182 and Cys-189, forming a small loop near the C-terminus. The DNA sequence that confirmed the amino acid sequence was reported by Martial et al (1979). Purified hGH is a white amorphous powder in its lyophilized form. It is readily soluble (concentrations>10 mg/L) in aqueous buffers at pH in a range of 6.5 to 8.5.

In solution, hGH exists predominantly as a monomer, with a small fraction as dimers and higher molecular weight oligomers. Under certain conditions, hGH can be induced to form larger amounts of dimers, trimers and higher oligomers.

Several derivatives of hGH are known, including naturally-occurring derivatives, variants and metabolic products, degradation products primarily of biosynthetic hGH and engineered derivatives of hGH produced by genetic methods. One example of a naturally-occurring derivative of hGH is GH-V, a variant of growth hormone found in the placenta. Other members of the gene locus are described in Chen et al (1989).

Methionyl hGH was the first form of hGH to be produced through recombinant DNA technology. This compound is actually a derivative of hGH having one additional methionine residue at its N-terminus (Goeddel et al, 1979).

A naturally-occurring variant of hGH called 20-K-hGH has been reported to occur in the pituitary as well as in the bloodstream (Lewis et al, 1978; Lewis et al, 1980). This compound, which lacks the 15 amino acid residues from Glu-32 to Gln-46, arises from an alternative splicing of the messenger ribonucleic acid (DeNoto et al, 1981). This compound shares many, but not all of the biological properties of hGH.

20-K-hGH is made in the pituitary and secreted into the blood. It makes up about 5% of growth hormone output of adults, and about 20% of growth hormone output of children. It has the same growth promoting activity as 22 kD growth hormone, and has been reported to have equal to or greater the amount of lipolytic activity as the 22 kD form. It binds to growth hormone receptors with equal affinity as the 22 kD growth hormone, and has one tenth the lactogenic (prolactin-like) bioactivity as the 22 kD hormone. Unlike 22 kD, the 20-k-hGH has weak anti-insulin activity.

A number of derivatives of hGH arise from proteolytic modifications of the molecule. The primary pathway for the metabolism of hGH involves proteolysis. The region of hGH around residues 130-150 is extremely susceptible to proteolysis, and several derivatives of hGH having nicks or deletions in this region have been described (Thorlacius-Ussing, 1987). This region is in the large loop of hGH, and cleavage of a peptide bond there results in the generation of two chains that are connected through the disulfide bond at Cys-53 and Cys-165. Many of these two-chain forms are reported to have increased biological activity (Singh et al, 1974). Many derivatives of human growth hormone have been generated artificially through the use of enzymes. The enzymes trypsin and subtilisin, as well as others, have been used to modify hGH at various points throughout the molecule (Lewis et al, 1977; Graff et al, 1982). One such derivative, called two-chain anabolic protein (2-CAP), was formed through the controlled proteolysis of hGH using trypsin (Becker et al, 1989). 2-CAP was found to have biological properties very distinct from those of the intact hGH molecule, in that the growth-promoting activity of hGH was largely retained and most of the effects on carbohydrate metabolism were abolished.

Asparagine and glutamine residues in proteins are susceptible to deamidation reactions under appropriate conditions. Pituitary hGH has been shown to undergo this type of reaction, resulting in conversion of Asn-152 to aspartic acid and also, to a lesser extent, conversion of Gln-137 to glutamic acid (Lewis et al, 1981). Deamidated hGH has been shown to have an altered susceptibility to proteolysis with the enzyme subtilisin, suggesting that deamidation may have physiological significance in directing proteolytic cleavage of hGH. Biosynthetic hGH is known to degrade under certain storage conditions, resulting in deamidation at a different asparagine (Asn-149). This is the primary site of deamidation, but deamidation at Asn-152 is also seen (Becker et al, 1988). Deamidation at Gln-137 has not been reported in biosynthetic hGH.

Methionine residues in proteins are susceptible to oxidation, primarily to the sulfoxide. Both pituitary-derived and biosynthetic hGH undergo sulfoxidations at Met-14 and Met-125 (Becker et al, 1988). Oxidation at Met-170 has also been reported in pituitary but not biosynthetic hGH. Both desamide hGH and Met-14 sulfoxide hGH have been found to exhibit full biological activity (Becker et al, 1988).

Truncated forms of hGH have been produced, either through the actions of enzymes or by genetic methods. 2-CAP, generated by the controlled actions of trypsin, has the first eight residues at the N-terminus of hGH removed. Other truncated versions of hGH have been produced by modifying the gene prior to expression in a suitable host. The first 13 residues have been removed to yield a derivative having distinctive biological properties (Gertler et al, 1986) in which the polypeptide chain is not cleaved.

Although human growth hormone was originally obtained from pituitary glands of cadavers, these preparations were not electrophoretically homogeneous, and antibodies appeared in the serum of patients treated with preparations of the order of 50% purity, the immunogenicity being attributed to inactive components. Recombinant DNA technology permitted production of an unlimited supply of hGH in a number of different systems. Purification of hGH from the culture medium is facilitated by the presence of only low amounts of contaminating proteins. In fact, it has been shown that hGH can be purified on a laboratory scale by a single purification step on a reversed-phase HPLC column (Hsiung et al (1989).

Recombinant human growth hormone, rhGH, is produced by Serono International S.A. as SEROSTIM®, which product has been given accelerated FDA approval for treating weight loss and wasting in AIDS patients. SAIZEN® is recombinant human growth hormone indicated for GH deficiency in children, for Turner syndrome in girls, as well as chronic renal failure in children. PROTROPIN®, produced by Genentech, Inc. (South San Francisco, Calif.), differs slightly in structure from natural sequence hGH, having an additional methionine residue at the N-terminus. Recombinant hGH is generally marketed as vials containing hGH plus additional excipients, e.g., glycine and mannitol, in a lyophilized form. A companion diluent vial is provided, allowing the patient to reconstitute the product to the desired concentration prior to administration of the dose. Recombinant hGH can also be marketed in other well-known manners, such as pre-filled syringes.

In order for hGH to be available commercially as a therapeutic, stable formulations must be prepared. Such formulations must be capable of maintaining activity for appropriate storage times and be acceptable for administration by patients.

Human GH has been formulated in a variety of ways. By way of example, U.S. Pat. No. 5,096,885 discloses a stable pharmaceutically acceptable formulation of hGH comprising, in addition to the hGH, glycine, mannitol, a buffer and optionally a non-ionic surfactant, the molar ratio of hGH:glycine being 1:50.

WO 93/19776 discloses injectable formulations of GH comprising citrate as buffer substance and optionally growth factors such as insulin-like growth factors or epidermal growth factor, amino acids such as glycine or alanine, mannitol or other sugar alcohols, glycerol and/or a preservative such as benzyl alcohol.

WO 94/101398 discloses a GH formulation containing hGH, a buffer, a non-ionic surfactant and, optionally, mannitol, a neutral salt and/or a preservative.

EP-0131864 describes an aqueous solution of proteins with molecular weight above 8500 daltons, which have been protected from adsorption at interfaces, against denaturing and against precipitation of the protein by addition of a linear polyoxyalkylene chain-containing surface-active substance as a stabilising agent.

EP-0211601 discloses a growth promoting formulation comprising an aqueous mixture of growth promoting hormone and a block copolymer containing polyoxyethylene-polyoxypropylene units and having an average molecular weight of about 1,100 to about 40,000 which maintains the fluidity of the growth promoting hormone and its biological activity upon administration.

WO 97/29767 discloses a liquid formulation comprising a growth hormone, trisodium citrate dihydrate, sodium chloride, sodium hydroxide, benzyl alcohol, Pluronic F-68, said formulation having a pH of 5.6.

U.S. Pat. No. 5,567,677 discloses liquid formulations comprising human growth hormone, sodium citrate, sodium phosphate, glycine, mannitol, optionally benzyl alcohol.

Pharmaceutical preparations of hGH tend to be unstable, particularly in solution. Chemically degraded species such as deamidated or sulfoxylated forms of hGH occur, and dimeric or higher molecular weight aggregated species may result from physical instability (Becker et al (1988); Becker et al., 1987; Pearlman and Nguyen (1989)).

As a consequence of the instability of hGH in solution, pharmaceutical formulations of hGH are generally in lyophilised form, which must then be reconstituted prior to use. Reconstitution is usually carried out by the addition of a pharmaceutically acceptable diluent such as sterile water for injection, sterile physiological saline or an appropriate sterile physiologically acceptable diluent.

Reconstituted solutions of hGH are preferably stored at 4° C. to minimise chemical and physical degradation reactions, however some degradation will occur during such storage which can be for a period of up to 14 days.

A pharmaceutical formulation of hGH provided in a liquid form, particularly one that maintains stability of hGH without formation of precipitation or aggregation or any other particulate matter over a prolonged period of time, would be particularly advantageous.

Therefore, it is an object of the present invention to provide liquid formulations of growth hormone that do not result in the formation of undesirable particulate matter and that has a prolonged storage time.

SUMMARY OF THE INVENTION

A first aspect of the invention relates to a liquid formulation comprising:
a) a growth hormone, or a substance, which stimulates release or potentiates the activity of endogenous hGH;
b) an alkali metal salt;
c) an alkaline earth metal salt or a pseudo alkaline earth metal salt; and
d) a citrate/phosphate buffer.

A second aspect of the invention relates to a process for preparing the liquid formulation in accordance with the present invention.

In a third aspect, the invention relates to a freeze-dried formulation which is reconstituted in such a way to give the new liquid formulation mentioned above.

In a third aspect, the invention relates to the use of a formulation according to the invention for mono-dose or multi-dose administration of a growth hormone.

A fourth aspect of the invention relates to a form of presentation of the liquid formulation according to the invention.

DETAILED DESCRIPTION OF THE INVENTION

In accordance with the present invention, it has been found that the chemical and physical stability of a growth hormone in a liquid formulation may be increased by a specific choice of mineral salts. Thus the obtained solutions may be stored for a prolonged period of time, e.g. for about 1 to 52 weeks, or 1 to 16, or 1 to 4 weeks, preferably at room temperature.

It has further been found that improved stability of growth hormone in liquid formulation over a prolonged period of time may be obtained with a composition according to claim 1.

Therefore, the invention relates to a liquid formulation comprising:
a) a growth hormone, or a substance, which stimulates release or potentiates the activity of endogenous hGH;
b) an alkali metal salt;
c) an alkaline earth metal salt or a pseudo alkaline earth metal salt; and
d) a citrate/phosphate buffer.

In one embodiment, the liquid formulations of the present invention may be used for multi-dose administration, whereby said formulation may be stored at room temperature for a period of 1 week or more.

Growth hormone that may be formulated in accordance with the present invention may be derived from any species, such as bovine, porcine, canine or feline, depending on the intended use of the formulation. A substance, which stimulates release or potentiates the activity of endogenous hGH, is e.g. growth hormone releasing hormone.

Preferably, the following substances may be formulated in accordance with the present invention:
a) human growth hormone;
b) a fragment of (a) which has agonistic activity on the hGH receptor;
c) a variant of (a) or (b) which has at least 70% sequence identity with (a) or (b) and which has agonistic activity on the hGH receptor;
d) a variant of (a) or (b) which is encoded by a DNA sequence which hybridizes to the complement of the native DNA sequence encoding (a) or (b) under moderately stringent conditions and which has agonistic activity on the hGH receptor; or
e) a salt or functional derivative of (a), (b), (c) or (d) which has agonistic activity on the hGH receptor.

A formulation comprising human growth hormone is preferred in accordance with the present invention.

The term "human growth hormone", or "hGH", as used in the present invention, is intended to include the naturally-occurring and synthetic derivatives, as noted above, including, without limitation, both the 20 kD and the 22 kD human growth hormone, GH-V, and other members of the growth hormone gene locus, as described in detail in the "Background of the invention".

The hGH may be naturally-occurring human growth hormone, or it may preferably be recombinant hGH. Recombinant GH may be expressed in any suitable host, either a prokaryotic, or a eukaryotic host. E. coli is a host particularly suitable for expression of hGH, for instance. Yeast, insect, or mammalian cells are further suitable for expression of recombinant growth hormone. Preferably, the hGH is expressed in human or animal cells, e.g. in Chinese Hamster Ovary (CHO) cells.

The term "hGH" or "growth hormone", as used herein, also includes functional derivatives, fragments, variants, analogs, or salts which retain the biological activity of growth hormone, i.e., which act as agonists to the growth hormone receptor. In other words, they are capable of binding to the growth hormone receptor to initiate the signaling activity of the receptor.

The term "functional derivatives", or "chemical derivatives", as used herein covers derivatives which may be prepared from the functional groups which occur as side chains on the residues of the N-or C-terminal groups, by means known in the art, and are included in the invention as long as they remain pharmaceutically acceptable, and do not destroy the biological activity of hGH as described herein, i.e., the ability to bind the hGH receptor and initiate receptor signaling, and do not confer toxic properties on compositions containing it. Derivatives may have chemical moieties, such as carbohydrate or phosphate residues, provided such a derivative retains the biological activity of hGH and remains pharmaceutically acceptable.

For example, derivatives may include aliphatic esters of the carboxyl groups, amids of the carboxyl groups by reaction with ammonia or with primary or secondary amines, N-acyl derivatives or free amino groups of the amino acid residues formed with acyl moieties (e.g., alkanoyl or carbocyclic aroyl groups) or O-acyl derivatives of free hydroxyl group (e.g., that of seryl or threonyl residues) formed with acyl moieties. Such derivatives may also include for example, polyethylene glycol side-chains, which may mask antigenic sites and extend the residence of the molecule in body fluids.

A growth hormone that has been derivatized or combined with a complexing agent may be long lasting. Therefore, a preferred embodiment of the invention relates to PEGylated versions of human growth hormone. Growth hormones genetically engineered to exhibit long lasting activity in the body, are also examples for hGH derivatives within the scope of the present invention.

hGH that is acetylated at the N-terminus has been isolated and identified (Lewis et al, 1979). It is not clear if acylation serves a regulatory role or is simply an artifact of the purification. However, it is expected that this molecule exhibits GH activity in a similar fashion to other hGH derivatives. Therefore, in a preferred embodiment, the invention relates to human growth hormone which is acetlyated at its N-terminus.

Preferably, the formulation according to the invention comprises a dimer of human growth hormone selected from the group consisting of a disulfide dimer connected through interchain disulfide bonds, a covalent irreversible non-disulfide dimer, a non-covalent dimer, and mixtures thereof.

The term "salts" herein refers to both salts of carboxyl groups and to acid addition salts of amino groups of the hGH molecule or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of hGH relevant to the present invention, i.e., the ability to bind to the hGH receptor and initiate receptor signaling.

In a further preferred embodiment, the invention relates to fragment of human growth hormone.

A "fragment" of the growth hormone according to the present invention refers to any subset of the molecule, that is, a shorter peptide, which retains the desired biological activity. Fragments may readily be prepared by removing amino acids from either end of the hGH molecule and testing the resultant for its properties as an hGH receptor agonist. Proteases for removing one amino acid at a time from either the N-terminal or the C-terminal of a polypeptide are known, and so determining fragments which retain the desired biological activity involves only routine experimentation.

Preferably, hGH fragments in accordance with the present invention may have internal deletions, as long as the deletion does not affect the biological activity of hGH, i.e. binding to and initiating signaling through the hGH receptor. A fragment that is preferred according to the invention lacks 15 amino acids from Glutamic acid (Glu) 32 to Glutamic acid 46.

hGH fragments may further be truncated at the C- or N-terminus. Truncated hGH lacking the first eight N-terminal residues or the first 13 N-terminal residues of human growth hormone are also preferred in accordance with the present invention.

A short C-terminal hGH fragment had been described to retain a biological activity of hGH, see U.S. Pat. No. 5,869,452. Therefore, the use of a C-terminal fragment of hGH is preferred according to the invention. Fragment hGH177-191, comprising at least amino acid residues 177 to 191 of hGH (LRIVQCRSVEGSCGF) is particularly preferred in accordance with the present invention. Further preferred are derivatives of this peptide, such as the peptide variants described in U.S. Pat. No. 6,335,319 or WO99/12969, e.g. cyclic peptides.

Additionally, the polypeptide, which has such hGH receptor agonist activity, be it hGH, an analog or variant, salt, functional derivative or fragment thereof, can also contain additional amino acid residues flanking the hGH polypeptide. As long as the resultant molecule retains the hGH receptor agonist ability of the core polypeptide, one can determine whether any such flanking residues affect the basic and novel characteristics of the core peptide, i.e., its receptor agonist characteristics, by routine experimentation.

An example for such a GH variant, which is preferred in accordance with the present invention, is methionyl human growth hormone (Met-hGH), which has an additional methionine residue at the N-terminus of human growth hormone.

Variants of hGH, which are preferred according to the invention, comprise methionyl hGH, which is a human growth hormone having an additional methionine residue at its N-terminus. A further preferred variant is a human growth hormone lacking 15 amino acid residues from Glu32 to Glu46.

A "variant" of the human growth hormone according to the present invention refers to a molecule, which is substantially similar to either the entire protein or a fragment thereof. A variant may also be called a "mutein". A variant may e.g. be an isoform of hGH, such as a variant generated by alternative splicing. Variant (poly)peptides may also be conveniently prepared by direct chemical synthesis of the variant peptide, using methods well known in the art. Of course, a variant human growth hormone would have at least similar hGH receptor binding and signal initiating activity as hGH and which would, therefore, be expected to have similar activity to hGH.

Amino acid sequence variants of the human growth hormone can be prepared by mutations in the DNAs, which encode the synthesized human growth hormone derivatives. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame.

At the genetic level, these variants may be prepared by site-directed mutagenesis (as exemplified by Adelman et al, 1983) of nucleotides in the DNA encoding the peptide molecule, thereby producing DNA encoding the variant, and thereafter expressing the DNA in recombinant cell culture. The variants typically exhibit at least the same qualitative biological activity as the non-variant peptide.

An "analog" of human growth hormone according to the present invention refers to a non-natural molecule, which is substantially similar to either the entire molecule or to an active fragment thereof. An analog of human growth hormone useful in the present invention would exhibit GH activity.

The types of substitutions which may be made in the human growth hormone according to the present invention may be based on analysis of the frequencies of amino acid changes between a homologous protein of different species. Based upon such analysis, conservative substitutions may be defined herein as exchanges within one of the following five groups:

I. Small, aliphatic, nonpolar or slightly polar residues:
   Ala, Ser, Thr, Pro, Gly
II. Polar, negatively-charged residues and their amides:
   Asp, Asn, Glu, Gln
III. Polar, positively-charged residues:
   His, Arg, Lys
IV. Large, aliphatic non-polar residues:
   Met, Leu, Ile, Val, Cys
V. Large aromatic residues:
   Phe, Try, Trp Within the foregoing groups, the following substitutions are considered to be "highly conservative":
Asp/Glu
His/Arg/Lys
Phe/Tyr/Trp
Met/Leu/Ie/Val Semi-conservative substitutions are defined to be exchanges between two of groups (I)-(IV) above which are limited to supergroup (A), comprising (I), (II), and (III) above, or to supergroup (B), comprising (IV) and (V) above. Substitutions are not limited to the genetically encoded or even the naturally-occurring amino acids. When the epitope is prepared by peptide synthesis, the desired amino acid may be used directly. Alternatively, a genetically encoded amino acid may be modified by reacting it with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxylmethyl or carboxyamidomethyl derivatives. Cysteinyl residues also are derivatized by reaction with bromotrifluoroacetone, alpha-bromo-beta-(5-imidazoyl)propionic acid, chloroacetyl phosphate, N-alkylmaleimides, 3-nitro-2-pyridyl disulfide, methyl-2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5-7.0 because this agent is relatively specific for the histidyl side chain. Parabromophenacyl bromide is also useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino acid-containing residues include imidoesters such as methyl picolinimidate; pyridoxal phosphate; pyridoxal; chloroborohydride; trinitrobenzenesulfonic acid; O-methyliosurea; 2,4-pentanedione; and transaminase-catalyzed reaction with glyoxylate.

Arginyl residues are modified by reaction with one or several conventional reagents, among them phenylglyoxal; 2,3-butanedione; and ninhydrin. Derivatization of arginine residues requires that the reaction be performed in alkaline conditions because of the high pKa of the guanidine functional group. Furthermore, these reagents may react with the groups of lysine, as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidazole and tetranitromethane are used to form O-acetyl tyrosyl species and ε-nitro derivatives, respectively.

Carboxyl side groups (aspartyl or glutamyl) are selectively modified by reaction with carbodiimides (R'N—C—N—R') such as 1-cyclohexyl-3-[2-morpholinyl-(4-ethyl)]carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Examples of production of amino acid substitutions in proteins which can be used for obtaining analogs of the hGH for use in the present invention include any known method steps, such as presented in U.S. Pat. Nos. RE 33,653; 4,959,314; 4,588,585 and 4,737,462, to Mark et al; U.S. Pat. No. 5,116,943 to Koths et al; U.S. Pat. No. 4,965,195 to Namen et al; and U.S. Pat. No. 5,017,691 to Lee, et al, and lysine substituted proteins presented in U.S. Pat. No. 4,904,584 (Shaw et al). Further growth hormone variants have been described e.g. in U.S. Pat. No. 6,143,523 (Cunningham et al.).

Among the substances which bind to and initiate signaling of the human growth hormone receptor which may be used in accordance with the present invention are all of those growth hormone analogs and mimetics already known in the literature, such as, for example, those disclosed in U.S. Pat. Nos. 5,851,992; 5,849,704; 5,849,700; 5,849,535; 5,843,453; 5,834,598; 5,688,666; 5,654,010; 5,635,604; 5,633,352; 5,597,709; and 5,534,617.

Preferably, the hGH variant or analog will have a core sequence, which is the same as that of the native sequence or biologically active fragment thereof, which has an amino acid sequence having at least 70% identity to the native amino acid sequence and retains the biological activity thereof. More preferably, such a sequence has at least 80% identity, at least 90% identity, or most preferably at least 95% identity to the native sequence.

"Identity" reflects a relationship between two or more polypeptide sequences or two or more polynucleotide sequences, determined by comparing the sequences. In general, identity refers to an exact nucleotide to nucleotide or amino acid to amino acid correspondence of the two polynucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences, to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al., 1984), for example the programs BESTFIT and GAP, may be used to determine the % identity between two polynucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at www.ncbi.nm.nih.gov) and FASTA (Pearson W R, 1990; Pearson 1988).

Preferred changes for variants or muteins in accordance with the present invention are what are known as "conservative" substitutions. Conservative amino acid substitutions of growth hormone polypeptides or proteins, may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Analogs or variants in accordance with the present invention may also be determined in accordance with the following procedure. The DNA of the native sequence is known to the prior art and is found in the literature (Martial et al, 1979). Polypeptides encoded by any nucleic acid, such as DNA or RNA, which hybridizes to the complement of the native DNA or RNA under highly stringent or moderately stringent conditions, as long as that polypeptide maintains the biological activity of the native sequence, are also considered to be within the scope of the present invention.

Stringency conditions are a function of the temperature used in the hybridization experiment, the molarity of the monovalent cations and the percentage of formamide in the hybridization solution. To determine the degree of stringency involved with any given set of conditions, one first uses the equation of Meinkoth et al. (1984) for determining the stability of hybrids of 100% identity expressed as melting temperature Tm of the DNA-DNA hybrid:

$$Tm=81.5° C.+16.6(_{Log}M)+0.41(\% GC)-0.61(\% form)-500/L$$

where M is the molarity of monovalent cations, % GC is the percentage of G and C nucleotides in the DNA, % form is the percentage of formamide in the hybridization solution, and L is the length of the hybrid in base pairs. For each 1° C. that the Tm is reduced from that calculated for a 100% identity hybrid, the amount of mismatch permitted is increased by about 1%. Thus, if the Tm used for any given hybridization experiment at the specified salt and formamide concentrations is 10° C. below the Tm calculated for a 100% hybrid according to equation of Meinkoth, hybridization will occur even if there is up to about 10% mismatch.

As used herein, highly stringent conditions are those which are tolerant of up to about 15% sequence divergence, while moderately stringent conditions are those which are tolerant of up to about 20% sequence divergence. Without limitation, examples of highly stringent (12-15° C. below the calculated Tm of the hybrid) and moderately (15-20° C. below the calculated Tm of the hybrid) conditions use a wash solution of 2×SSC (standard saline citrate) and 0.5% SDS at the appropriate temperature below the calculated Tm of the hybrid. The ultimate stringency of the conditions is primarily due to the washing conditions, particularly if the hybridization conditions used are those, which allow less stable hybrids to form along with stable hybrids. The wash conditions at higher stringency then remove the less stable hybrids. A common hybridization condition that can be used with the highly stringent to moderately stringent wash conditions described above is hybridization in a solution of 6×SSC (or 6×SSPE), 5× Denhardt's reagent, 0.5% SDS, 100 µg/ml denatured, fragmented salmon sperm DNA at a temperature approximately 20° to 25° C. below the Tm. If mixed probes are used, it is preferable to use tetramethyl ammonium chloride (TMAC) instead of SSC (Ausubel, 1987-1998).

While the present invention provides recombinant methods for making the human growth hormone derivatives, these derivatives may also be made by conventional protein synthesis methods which are well known to those skilled in the art.

The formulation of the invention comprises polyethylene-polypropylene glycol. This polymer is a nonionic surfactant. A surfactant may herein also be called "tensioactive" or "tensioactive agent". In yet a further preferred embodiment, the formulation comprises the polyethylene-polypropylene glycol in a concentration ranging from 0.5 to 5 mg/ml or 1 to 2 mg/ml or 1.5 mg/ml.

In a preferred formulation, the surfactant is a pluronic polyol, such as for instance F68. Pluronic F68 is highly preferred in accordance with the present invention.

By formulating GH with the surfactant Pluronic® F68 (BASF, also known as Poloxamer 188) a stable formulation was obtained that avoids the problem of precipitation, aggregation or generation of particulate matter of any kind.

Pluronic F68 is a block copolymer of ethylene oxide (EO) and propylene oxide (PO). The propylene oxide block (PO) is sandwiched between two ethylene oxide (EO) blocks.

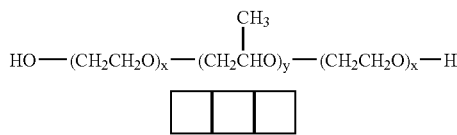

1. A hydrophobe of the desired molecular weight is created by the controlled addition of propylene oxide to the two hydroxyl groups of propylene glycol; and
2. Ethylene oxide is added to sandwich the hydrophobe between hydrophilic groups.

In Pluronic F68, the percentage of polyoxyethylene (hydrophile) is 80%, and the molecular weight of the hydrophobe (polyoxypropylene) is approximately 1967 Da.

Typical properties of Pluronic F68 are listed below:
Average Molecular Weight: 8400;
Melt/pour point: 52° C.;
Physical Form @ 20° C.: solid;
Viscosity (Brookfield) cps: 1000 [liquids at 25° C., pastes at 60° C. and solids at 77° C.];
Surface tension, dynes/cm at 25° C.;
0.1% Conc.: 50.3
0.01% Conc.: 51.2
0.001% Conc.: 53.6
Interfacial tension, dynes/cm at 25° C. vs Nujol;
0.1% Conc.: 19.8
0.01% Conc.: 24.0
0.01% Conc.: 26.0
Draves Wetting, Seconds 25° C.
1.0% Conc.: >360
0.1% Conc.: >360
Foam Height
Ross Miles, 0.1%, mm at 50° C.: 35
Ross Miles, 0.1%, mm at 26° C.: 40
Dynamic, 0.1%, mm at 400 ml/min: >600
Cloud point in aqueous solution, ° C.
1% Conc.: >100
10% Conc.: >100
HLB (hydrophile-lipophile balance): 29

Other polymers having properties similar to Pluronic F68 may also be used in the formulations of the invention.

The polyethylene-polypropylene glycol may be used in a concentration ranging from 0.5 to 5 mg/ml or 1 to 2 mg/ml or 1.5 mg/ml.

The person skilled in the art will appreciate that one or more further surfactants may be used in addition to polyethylene-polypropylene glycol.

The formulation of the invention further comprises a stabilizing agent. A stabilizing agent may also act as an isotonicity agent.

An "isotonicity agent" is a compound that is physiologically tolerated and imparts a suitable tonicity to a formulation to prevent the net flow of water across cell membranes that are in contact with the formulation. Compounds such as glycerin, are commonly used for such purposes at known concentrations. Other suitable stabilizing agents include, but are not limited to, amino acids or proteins (e.g. glycine or albumin), salts (e.g., sodium chloride), and sugars (e.g., dextrose, sucrose and lactose).

Stabilizing agents (stabilizer) or isotonicity agents that maybe preferably used in accordance with the present invention include non-reducing sugars, including sucrose, trehalose, sorbose, melezitose and raffinose. Mannitol, xylitol, erythritol, threitol, sorbitol and glycerol.

In a preferred embodiment, the stabilizer or isotonicity agent is sucrose.

In a further preferred embodiment, the formulation has sucrose in a concentration ranging from 10 mg/ml to 100 mg/ml or 20 mg/ml to 80 mg/ml or about 60 mg/ml.

The formulations according to the present invention contain an alkali metal salt, including NaCl, KCl, $Na_2SO_4$, $Na_2CO_3$. In a preferred embodiment the alkali metal salt is NaCl or $Na_2SO_4$.

The formulations according to the present invention contain furthermore an alkaline earth metal salt including $CaCl_2$, $MgCl_2$, $MgSO_4$, $(NH_4)_2CO_3$. In a preferred embodiment the earth alkaline salt is $MgCl_2$.

The formulations of the invention further comprise a citrate/phosphate buffer. A citrate/phosphate buffer that may be used within the present invention may e.g. be sodium citrate/sodium phosphate buffer.

The term "buffer" or "physiologically-acceptable buffer" refers to solutions of compounds that are known to be safe for pharmaceutical or veterinary use in formulations and that have the effect of maintaining or controlling the pH of the formulation in the pH range desired for the formulation.

It is preferred that the formulations of the present invention comprise citrate/phosphate in a concentration ranging from 1 to 100 mM or from 5 to 50 mM or from 10 to 20 mM.

In accordance with the present invention, it is preferred that the pH of the formulation is in the range of 5 to 7 or 5.5 to 6.5 or at or about 6. More preferably, the pH is from 5.5 to 5.9.

The formulations of the invention are liquid and comprise therefore an aqueous diluent.

The term "aqueous diluent" refers to a liquid solvent that contains water. Aqueous solvent systems may consist solely of water, or may consist of water as well as one or more miscible solvents, and may contain dissolved solutes such as sugars, buffers, salts or other excipients.

The formulation may also comprise one or more non-aqueous solvents. Commonly-used non-aqueous solvents are the short-chain organic alcohols, such as, methanol, ethanol, propanol, short-chain ketones, such as acetone, and poly alcohols, such as glycerol.

The formulation of the invention preferably further comprises a preservative. Addition of a preservative is especially preferred if growth hormone is intended for multi-dose administration.

A "preservative" is a compound, which can be included in the formulation to essentially reduce bacterial action therein, thus facilitating the production of a multi-use formulation, for example. Examples of potential preservatives include octadecyldimethyl-benzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl paraben such as methyl or propyl paraben, catechol, resorcinol, cyclohexanol, 3-pentanol, and m-cresol.

A preservative may also be a bacteriostatic herein. The term "bacteriostatic" refers to a compound or compositions added to a formulation to act as an anti-bacterial agent. A preserved GH containing formulation of the present invention preferably meets statutory or regulatory guidelines for preservative effectiveness to be a commercially viable multi-use (multi-dose) product. Examples of bacteriostatics include phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal.

Preferable, the preservative is present in a concentration ranging from 1 to 10 mg/ml or 2 to 5 mg/ml or 3 mg/ml.

The preferred preservative of the invention is phenol.

In a second aspect, the invention relates to a process for production of the liquid formulation comprising the step of preparing an aqueous solution of the components of the formulation in accordance with the present invention.

The invention further relates to a process for production of the liquid formulation comprising the step of placing a predetermined amount of the formulation into a sterile container. Typically, such an amount is in the milliliter range.

Liquid formulations of hGH for therapeutic administration may also be prepared by combining hGH and stabilizing agents having the desired degree of purity with physiologically acceptable excipients, buffers or preservatives (Remington's Pharmaceutical Sciences, 16th Edition, Osoll A. Ed (1 980). Acceptable excipients are those, which are nontoxic to the patient at the concentrations and dosages employed, and include e.g. buffers, preservatives, antioxidants, pH and tonicity modifiers.

The liquid formulation of growth hormone may also include one or more other stabilizing excipients if desired. Additional stabilizing excipients may include, for example, amino acids such as glycine or alanine, mannitol or other sugar alcohols, or glycerol. In addition, the liquid formulation may include other growth factors such as insulin-like growth factors or IGF-binding proteins.

The increased stability of hGH provided by the formulation prepared in accordance with the present invention permits a wider use of hGH formulations that may be more concentrated than those commonly in use.

The term "stability" refers to the physical, chemical, and conformational stability of formulations of growth hormone of the present invention (including maintenance of biological potency). Instability of a protein formulation may be caused by chemical degradation or aggregation of the protein molecules to form higher order structures, by deglycosylation, modification of glycosylation, deamidation, oxidation or any other structural modification that reduces at least one biological activity of a GH polypeptide included in the present invention.

Auto-injectors are known in the art, such as the one called Easyject®, which is particularly useful for administration of hGH. Needle-free administration may also be used in connection with the present invention, using special devices that are known in the art.

A further aspect of the invention relates to a pharmaceutical composition comprising the formulation of the invention. Compositions within the scope of this invention include all compositions comprising at least one human growth hormone or derivative, analog, or variant thereof according to the present invention in an amount effective to achieve its intended purpose. While individual needs vary, determination of optimal ranges of effective amounts of each component is within the skill of the art. Typical dosages comprise about 0.001 to about 0.1 mg/kg body weight per day. When administered to patients, the hGH therapy may be administered concomitantly with other therapies which may be indicated in this disease.

The liquid formulation of the present invention may be obtained upon reconstitution of a freeze dried sample of Growth Hormone in a suitable diluent (e.g. water for injection) in such a way that the formulation contains the excipients identified above.

The term "administer" or "administering" means to introduce a formulation of the present invention into the body of a patient in need thereof to treat a disease or condition.

In a preferred embodiment of the invention, hGH is administered in a daily dosage of about 0.1 to 10 mg or about 0.5 to 6 mg. In one embodiment the daily dosage is abvout 0.15-0.3 mg of hGH per day, preferably by subcutaneous injection. In a further embodiment a dosage of about 1 mg of human growth hormone is administered per day to a patient in need of.

In a further embodiment, hGH is administered at alternating dosages, the first dosage being higher than the second dosage. Preferably, the first dosage is about 1 mg and the second dosage is about 0.5 mg. Weekly dosages are preferably about 6 mg or about 5 mg or about 4.5 mg, depending on the needs of the patient.

The term "patient" means a mammal that is treated for a disease or condition. Patients are of, but not limited to, the following origin, human, ovine, porcine, equine, bovine, rabbit and the like.

The formulation of the present invention is suitable for many different administration regimens. For example, administration can be by parenteral, such as subcutaneous, intravenous, intramuscular, oral, intraperitoneal, aerosol, transdermal, intrathecal, or rectal routes. The dosage administered depends upon the age, health and weight of the recipient, type of previous or concurrent treatment, if any, frequency of the treatment and the nature of the effect desired.

In accordance with the present invention, preferred administration routes are the subcutaneous and the intramuscular routes.

It is understood that the suitable dose of a composition or formulation according to the present invention will depend upon the age, health and weight of the recipient, kind of concurrent treatment, if any, frequency of treatment, and the nature of the effect desired. However, the most preferred dosage can be tailored to the individual subject, as is understood and determinable by one of skill in the art, without undue experimentation. This typically involves adjustment of a standard dose, e.g., reduction of the dose if the patient has a low body weight.

The total dose required for each treatment may be administered in multiple doses (multi-dose) or in a single dose ("mono-dose").

The expression "multi-dose use" is intended to include the use of a single vial, ampoule or cartridge of GH formulation for more than one injection, for example 2, 3, 4, 5, 6 or more injections. The injections may be spaced in time, for example, by a period of 6, 12, 24, 48 or 72 hours.

The invention further relates to the use of a formulation in accordance with the present invention for mono-dose administration. In an alternative aspect, the invention relates to the use of a formulation in accordance with the present invention for multi-dose administration.

Typical hGH multidose formulations of Serono (Saizen) contain 1.33, 3.33 or 8 mg of hGH.

Typical hGH multidose formulations of Lilly (Humatrope) contain 6, 12 or 24 mg of hGH.

Typical hGH multidose formulations of Pfizer (Genotropin) contain 5 or 12 mg of hGH.

Typical hGH multidose formulations of Novo Nordisk (Genotropin) contain 5, 10 or 15 mg of hGH.

Thus, in typical formulations the hGH amount provided in a vial is 1.33, 3.33, 5, 6, 8, 10, 12, 15 or 24 mg.

The compositions may be administered alone or in conjunction with other therapeutics directed to the disease or directed to other symptoms thereof.

hGH formulations of the present invention may be dispensed into vials. The term "vial" refers broadly to a reservoir suitable for retaining GH in solid or liquid form in a contained sterile state. Examples of a vial as used herein include ampoules, cartridges, blister packages, or other such reservoir suitable for delivery of the GH to the patient via syringe, pump (including osmotic), catheter, transdermal patch, pulmonary or transmucosal spray. Vials suitable for packaging products for parenteral, pulmonary, transmucosal, or transdermal administration are well-known and recognized in the art.

The increased stability of hGH formulations permits long term storage at an appropriate temperature, such as below freezing (e.g. at −20° C.), or above freezing, preferably at 2-8° C., most preferably at +5° C., or even at room temperature, e.g. at +25° C.

Formulations of hGH to be used for in vivo administration must be sterile. This may e.g. be readily accomplished by filtration through sterile filtration membranes.

Therapeutic hGH liquid formulations generally are placed into a container having a sterile access port, for example, an intravenous solution bag or vial having a stopper which can be pierced by a hypodermic injection needle.

Therefore, a further aspect of the invention relates to a form of presentation of the liquid formulation of the invention hermetically closed in a sterile condition within a container suited for storage before use.

The formulations of the present invention may be used for the treatment of GH deficiency in children, weight loss and wasting in AIDS patients, for Turner syndrome in girls, as well as chronic renal failure in children.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Having now described the invention, it will be more readily understood by reference to the following example of an exemplary clinical study outline, that is provided by way of illustration, and not intended to be limiting of the present invention.

EXAMPLE

The following 2 formulations were assessed in terms of their stability:

Formulation A:

| Ingredients | Formulation A |
|---|---|
| r-hGH (mg/ml) | 8.0 |
| Sodium citrate phosphate pH 5.8 (mM) | 5.0 |
| Sodium sulfate (mM) | 100.0 |
| Magnesium chloride (mM) | 50 |
| Phenol (mg/ml) | 3.0 |
| Pluronic F68 (mg/ml) | 1.5 |

Formulation B:

| Ingredients | Formulation B |
|---|---|
| r-hGH (mg/ml) | 8.0 |
| Sodium citrate phosphate pH 5.57 (mM) | 5.0 |
| Sodium chloride (mM) | 171.0 |
| Magnesium chloride (mM) | 5 |
| Phenol (mg/ml) | 3.0 |
| Pluronic F68 (mg/ml) | 0.2 |

The chemical stability of Formulations A & B was assessed after a storage of the samples at a temperature of 40° C. over a prolonged period of time, i.e. after 3 weeks.

The stability of hGH was determined by RP-HPLC (reverse phase HPLC). Thereby, the amount of unchanged, intact growth hormone was derived from the degree of change of the main peak of the human growth hormone. On other words, the degree of change was inferred from the change of the main peak of the human growth hormone and calculated as percentage of unchanged r-hGH versus the corresponding peak at time zero.

Results:

Formulation A:
  After storing the sample for 1 month at 40° C., the main peak measured for r-hGH represents 62% of the corresponding peak at time zero (i.e. 62% of unchanged r-hGH is found after a 1 month storage at 40° C.).
  After 1 month of storage at room temperature (25° C.), the main peak measured for r-hGH represents 91% of the corresponding peak at time zero (i.e. 91% of unchanged r-hGH is found after a 1 month storage at 25° C.).

Formulation B:
  After 3 weeks of storage at 40° C., the main peak measured for r-hGH represents 69% of the corresponding peak at time zero (i.e. 69% of unchanged r-hGH is found after a 3 weeks storage at 40° C.).

REFERENCES

1. Altschul S F et al, J Mol Biol, 215, 403-410, 1990
2. Altschul S F et al, Nucleic Acids Res., 25:389-3402, 1997

3. Ausubel et al, Current Protocols in Molecular Biology, Greene Publications and Wiley Interscience (New York, 1987-1998)
4. Becker et al, Biotechnol. Appl. Biochem. 10:326 (1988)
5. Bewly et al, Int. J. Peptide and Protein Res. 4:281-287 (1972)
6. Chen et al, Genomics 4:479-497 (1989)
7. Devereux J et al, Nucleic Acids Res, 12, 387-395, 1984.
8. Gertler et al, Endocrinology 118:720 (1986)
9. Goeddel et al Nature, 281:544 (1979)
10. Graff et al, J. Biol. Chem. 257:2365 (1982)
11. Grantham, Science, Vol. 185, pp. 862-864 (1974).
12. Hsiung et al, Biotechnology 7:267 (1989)
13. Lewis et al, Endocrinology 101:1587 (1977)
14. Lewis et al, J. Biol. Chem. 253:2679 (1978)
15. Lewis et al, Endocrinology 104:1256 (1979)
16. Lewis et al, Biochem. Biophys. Res. Comm. 92:511 (1980)
17. Lewis et al, J. Biol. Chem. 256:11645 (1981)
18. Martial et al, Science 205:602-607 (1979)
19. Meinkoth J, Wahl G. Hybridization of nucleic acids immobilized on solid supports. Anal Biochem. May 1, 1984; 138(2):267-84.
20. Pearson W R, Methods in Enzymology, 183, 63-99, 1990
21. Pearson W R and Lipman D J, Proc Nat Acad Sci USA, 85, 2444-2448, 1988
22. Pearlman and Nguyen (1989), In D. Marshak and D. Liu (eds), Therapeutic Peptides and Proteins, Formulations, Delivery and Targeting, Current Communications in Molecular Biology, Cold-Spring Harbour Laboratory, Cold SpringHarbour, N.Y., pp 23-30
23. Singh et al, Endocrinology 94:883 (1974)
24. Smith et al, Science 260:1640-1643 (1998)
25. Smith and Waterman J Mol Biol, 147, 195-197, 1981, Advances in Applied Mathematics, 2, 482-489, 1981
26. Thorlacius-Ussing, Neuroendocrinology 43:233 (1987)
27. WO 93/19776
28. WO 94/101398
29. EP-0131864
30. EP-0211601
31. WO 97/29767
32. U.S. Pat. No. 5,567,677

The invention claimed is:

1. A liquid formulation comprising
   a) growth hormone (GH) or a growth hormone releasing hormone (GHRH);
   b) an alkali metal salt;
   c) an alkaline earth metal salt or a pseudo alkaline earth metal salt; and
   d) a citrate/phosphate buffer.

2. The formulation according to claim 1, wherein the growth hormone is present as human growth hormone.

3. The formulation according to claim 1, wherein the growth hormone releasing hormone (GHRH) is present in the formulation.

4. The formulation according to claim 1, wherein the alkali metal salt is selected from the group consisting of NaCl, KCl, $Na_2SO_4$, $Na_2CO_3$.

5. The formulation according to claim 4, wherein the alkali metal salt is NaCl or $Na_2SO_4$.

6. The formulation according to claim 1, wherein the alkaline earth metal salt is selected from the group consisting of $CaCl_2$, $MgCl_2$, $MgSO_4$, $(NH_4)_2CO_3$.

7. The formulation according to claim 6, wherein the earth alkaline salt is $MgCl_2$.

8. The formulation according to claim 1, wherein the buffer is a sodium citrate/sodium phosphate buffer.

9. The formulation according to claim 8, wherein the buffer is in a concentration ranging from 1 to 100 mM or from 5 to 50 mM or from 10 to 20 mM.

10. The formulation according to claim 1, further comprising a surfactant.

11. The formulation according to claim 10, wherein the surfactant is a polyethylene-polypropylene glycol.

12. The formulation according to claim 11, wherein the surfactant is Pluronic F68.

13. The formulation according to claim 10 or 11, comprising the polyethylene-polypropylene glycol in a concentration ranging from 0.5 to 5 mg/ml or 1 to 2 mg/ml or 1.5 mg/ml.

14. The formulation according to claim 1, further comprising a stabilizer.

15. The formulation according to claim 14, wherein the stabilizer is sucrose.

16. The formulation according to claim 15, comprising sucrose in a concentration ranging from 10 mg/ml to 100 mg/ml or 20 mg/ml to 80 mg/ml or about 60 mg/ml.

17. The formulation according to claim 1 having a pH in the range of 5 to 7 or 5.5 to 6.5 or about 6.

18. The formulation according to claim 17, wherein the pH is in the range of 5.5-5.8.

19. The formulation according to claim 1, further comprising a preservative.

20. A formulation according to claim 19, comprising the preservative in a concentration ranging from 1 to 10 mg/ml or 2 to 5 mg/ml or 3 mg/ml.

21. The formulation according to claim 19 or 20, wherein the preservative is phenol.

22. The formulation according to claim 1, said formulation having a pH of 5.8 and consisting of r-hGH, sodium citrate/sodium phosphate, $Na_2SO_4$, $MgCl_2$, Phenol, Pluronic F 68, and optionally water for injection.

23. The formulation according to claim 1, said formulation having a pH of 5.8 and consisting of r-hGH, sodium citrate/sodium phosphate, NaCl, $MgCl_2$, Phenol, Pluronic F 68, and optionally water for injection.

24. A pharmaceutical composition comprising the formulation according to claim 1.

25. A form of presentation of the liquid formulation according to claim 1 hermetically closed in a sterile condition within a container suited for storage before use.

26. A method for treating GH deficiency in children, weight loss and wasting in AIDS patients, Turner syndrome in girls, or chronic renal failure in children, comprising administering the liquid formulation of claim 1 to a patient in need thereof.

27. The method of claim 26, wherein the liquid formulation is for mono-dose administration.

28. The method of claim 26, wherein the liquid formulation is for multi-dose administration.

* * * * *

UNITED STATES PATENT AND TRADEMARK OFFICE
CERTIFICATE OF CORRECTION

PATENT NO. : 7,662,393 B2 Page 1 of 1
APPLICATION NO. : 11/578136
DATED : February 16, 2010
INVENTOR(S) : Arvinte et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 227 days.

Signed and Sealed this

Thirtieth Day of November, 2010

David J. Kappos
*Director of the United States Patent and Trademark Office*